United States Patent [19]

Plummer et al.

[11] Patent Number: 4,888,486
[45] Date of Patent: Dec. 19, 1989

[54] SCANNING NUCLEAR CAMERA WITH AUTOMATIC ORBIT SHAPE MODIFICATION

[75] Inventors: Steven J. Plummer, Hudson; Antoine Ina, Richmond Hts., both of Ohio; David L. Tipping, Northford, Conn.; Peter D. Esser, Smithtown, N.Y.

[73] Assignee: Picker International, Inc., Highland Hts., Ohio

[21] Appl. No.: 246,675

[22] Filed: Sep. 20, 1988

[51] Int. Cl.$^4$ .............................................. G01T 1/166
[52] U.S. Cl. .................................. 250/363.04; 378/8; 378/95
[58] Field of Search ...................... 250/363.05, 363.08, 250/363.04; 378/8, 19, 20, 95

[56] References Cited

U.S. PATENT DOCUMENTS

| 4,400,620 | 8/1983 | Blum | 250/363.05 |
| 4,652,758 | 3/1987 | Barfod | 250/363.04 |

FOREIGN PATENT DOCUMENTS

| 0200939 | 11/1986 | European Pat. Off. | 250/363.04 |
| 0092975 | 6/1983 | Japan | 250/363.04 |

Primary Examiner—Carolyn E. Fields
Assistant Examiner—David P. Porta
Attorney, Agent, or Firm—Fay, Sharpe, Beall, Fagan, Minnich & McKee

[57] ABSTRACT

In preparation for a scan, a camera head (B) is positioned (30, 32, 34, 36) about a patient on a patient table (20) to determine the minor axis (54) and major axis (56). Based on a comparison (60) of a difference in the major and minor axes with preselected standards (62a, 62b, ...) one of a corresponding plurality of correction factor tables (64a, 64b, ...) is selected. During a scan as the camera head is rotated about the patient by an angular position clock (70). The radial distances of the camera head from the scan center are calculated (72, 74, 78) which cause the camera head to follow a generally ellipsoidal path. The size of the ellipse is adjusted (74, 78) in accordance with the major and minor axes. At each of a plurality of angular positions, the enabled correction factor table is addressed by the angular position and a corresponding correction factor is combined (80) with the radius. In this manner, the shape, as well as the size, of the orbit is adjusted.

15 Claims, 2 Drawing Sheets

SCANNING NUCLEAR CAMERA WITH AUTOMATIC ORBIT SHAPE MODIFICATION

BACKGROUND OF THE INVENTION

The present invention relates to the radiology arts. It finds particular utility in medical applications, specifically diagnostic imaging, and will be described with particular reference thereto. However, it is to be appreciated that the invention may have other applications including quality control monitoring, subject treatment, subject monitoring, and the like.

Heretofore, nuclear cameras have been mounted to image patients from a plurality of directions. With appropriate software, diagnostic data from radiation emanating from the patient was reconstructed into tomographic images. In order to obtain the appropriate data for tomographic reconstruction, the nuclear camera detector or head was rotated in a circular orbit around the patient.

Because patients normally do not have a circular aspect ratio, the camera head moved further than necessary from the patient during the circular orbit. To reduce the image degradation attributable to this excessive patient-to-camera distance, elliptical orbits were instituted. However, clearance between the corners of the patient table and the nuclear camera head necessitated a larger than otherwise necessary ellipse. In order to reduce the patient to nuclear camera distance still further, a peanut shaped orbit was developed. In the peanut shaped orbit, the nuclear camera detector came close to the patient at the top and bottom surfaces but moved further away to clear the table corners. The peanut shaped orbit was most easily programmed into a nuclear camera whose detector was mounted for generally circular rotation about the patient. For a nuclear camera gantry designed for rectilinear movement, e.g. horizontal translating movement and vertical translating movement, an orbit $r=b+a|\sin\S+z$ was developed. This orbit had larger lower lobes than upper lobes.

To facilitate automatic operation, the size of the above discussed orbit was selected by positioning the camera head at appropriate points along a selected orbit. Normally, the camera head was positioned with the appropriate clearance above, below, and to either side of the patient. The size of the orbit was adjusted to find the smallest orbit that would encompass all four of these camera head positions. In the orbit discussed above, the size of the orbit was changed by adjusting the size of the "a" and "b" terms. The z correction factor, which provided clearance for the table, remained fixed for all orbit sizes.

One of the problems with holding the z, or table clearance correction factor, constant is that the patient-to-detector head clearance was not optimized. The larger z correction factor necessary for larger orbits was excessively large at smaller orbits. Conversely, a smaller z correction factor, which would provide closer conformity of the camera head to the patient at small orbits, would result in a collision between the patient table and the camera head at larger orbits.

In accordance with the present invention, a new and improved method and apparatus are provided which changes both the size and the shape of the orbit.

SUMMARY OF THE INVENTION

In accordance with one aspect of the present invention, a tomographic camera system is provided. A camera head which receives radiation from a subject and produces output signals indicative thereof is movably supported on a gantry. A gantry control means controls movement of the camera head along a path of selected shape and size. A shape altering means automatically alters the camera head path shape in accordance with a characteristic of the subject. In accordance with the preferred embodiment, an image reconstruction means receives the output signals from the camera head and reconstructs a tomographic image representation therefrom.

In accordance with another aspect of the present invention, a method of scanning a patient is provided. A radiation detector is movable around a patient along a path with a preselected size and shape. A characteristic of the subject, such as height and width dimensions of a scanned region, are determined. The shape of the path is adjusted automatically in accordance with the measured subject characteristic.

A primary advantage of the present invention is that it reduces the average distance between a subject and the radiation detector.

Another advantage of the present invention is that it can accommodate a wide variety of subject sizes, including head scans, transverse torso scans, and the like.

Yet another advantage of the present invention is that it optimizes the portion of the orbit beneath the patient table.

Still further advantages of the present invention will become apparent upon reading and understanding of the following detailed description.

BRIEF DESCRIPTION OF THE DRAWINGS

The invention may take form in various parts and arrangements of parts or in various steps and arrangements of steps. The drawings are only for purposes of illustrating the preferred embodiment and are not to be construed as limiting the invention.

DETAILED DESCRIPTION OF THE PREFERRED EMBODIMENT

A gantry means A moves a camera head B around the periphery of a patient under the control of electronic control circuitry C. More specifically, the gantry means A includes a camera head angle positioning means 10 for angularly positioning the camera head. A first axis or vertical positioning means 12 positions the camera head along one axis and a second or longitudinal axis positioning means 14 positions the camera head along a second or longitudinal axis. Of course, rather than adjusting the camera head along rectilinear coordinates, the camera head could be positioned relative to polar coordinates or the like.

The camera head B, as is conventional in the art, includes a scintillation crystal which produces light scintillations in response to incident radiation. An array of photomultiplier tubes disposed adjacent the crystal to sense the scintillations. Position resolving circuitry determine a coordinate position and energy of each scintillation from the photomultiplier tubes response. Various linearity, uniformity, and other distortion correction circuitry may be provided as is conventional in the art.

The gantry means A causes the camera head B to rotate around a patient or subject disposed on a patient table 20. Preferably, the patient table is cantilevered from a base 22 in order to enable the camera head to move freely therearound.

Figure 2:
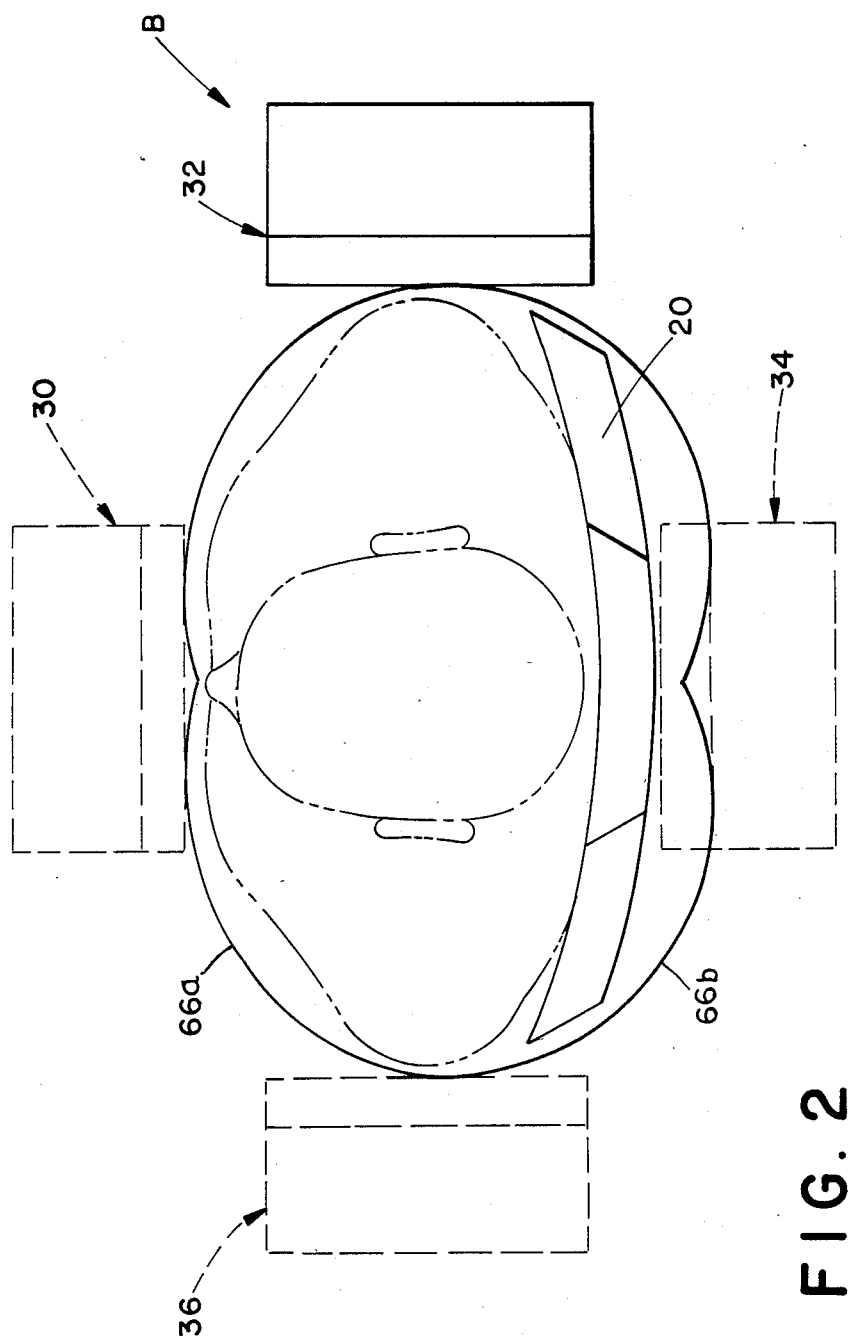

With reference to FIG. 2, in an initial set-up mode, the operator serially positions the camera head in a position 30 adjacent the top surface of the patient, a position 32 adjacent a side of the patient and patient support table, a position 34 adjacent the bottom surface of the patient support table, and a position 36 adjacent an opposite side portion of the patient and patient table. These four positions define the size of the path which the camera head B can follow about the patient without hitting the patient or patient table. Order of inputting positions is not critical. Also 0, 1, 2, 3, or 4 positions may be input, depending on how critical the orbit shape is for a given study. Where a position is not input, the stand microprocessor uses a default parameter.

Figure 1:
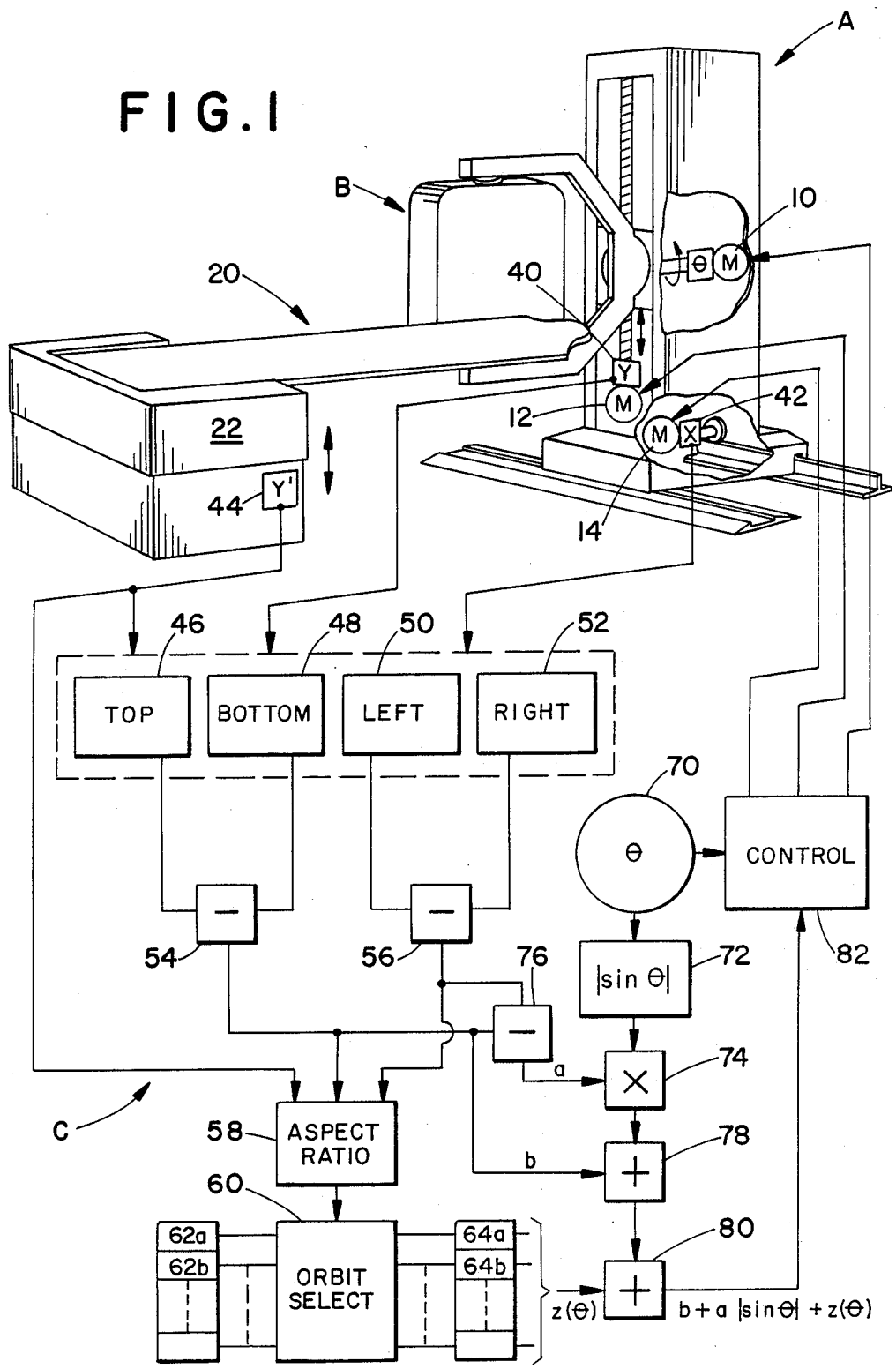
FIG. 1 is a diagrammatic illustration of a nuclear camera and control system in accordance with the present invention; and, FIG. 2 is a diagrammatic illustration of orbit shapes in accordance with the present invention.

Referring again to FIG. 1, a y or first axis encoder 40 and an x or second position encoder 42 provide an electronic output signal indicative of the coordinate position of the camera head. Optionally, a table height position means 44 may provide an output signal indicative of the height of the table. A top of the orbit memory means 46 stores the coordinate positions when the camera head is in position 30. A bottom of the orbit position means 48 stores the coordinates when the camera head is in the bottom position 34. Analogously, a left side memory means 50 and a right side memory means 52 store the coordinate positions when the camera is in the left and right side portions 32, 36, respectively.

A minor axis means 54 subtracts the coordinates of the top and bottom positions 30, 34 to determine the height of the orbit, i.e. minor axis. Optionally, the minor radius term may be determined as a function of the patient table height and the top of the path. A major axis means 56 subtracts the coordinates of the left and right side positions 32, 36 to determine the width or major axis of the orbit. An aspect ratio determining means 58 compares the height and width or major and minor diameters of the orbit. In the preferred embodiment, the orbit aspect ratio determining means subtracts the major and minor axes. Optionally, other comparisons, e.g. a ratio, may be made.

An orbit selecting means 60 compares the aspect ratio or degree of elongation of the orbit with a plurality of preselected standards from a standards memory means 62. The standard memory means 62 includes a memory cell 62a for storing a first standard, a memory cell 62b for storing a second standard, etc. The orbit selecting means 60 enables a corresponding correction or angular position dependent orbit shape modification factor table or memory 64a, 64b, etc. Each of the correction factors tables is preprogrammed with a plurality of orbit shaped adjusting correction factors. In the preferred embodiment, each correction factor table is addressable by the angular position 0 of the detector head relative to the patient. Optionally, other coordinate or detector head position location dependent systems may be utilized. The correction factors are iteratively selected and adjusted such that the orbit for each height to width difference comes as close to the patient and table surface as possible without directly interacting. The exact correction factors will vary with the gantry, camera head, and patient table selected.

In the preferred embodiment of FIG. 2, the camera head B is rotated such that it is always perpendicular to the center point of the orbit 66. The control circuit C adjusts the radius or distance the camera head is from the center point of the orbit as a function of the angular position $\theta$ of the camera head in its orbit around the patient. In the embodiment of FIG. 2, the radius r of the orbit 66 at any given angle $\theta$ is expressed by the equation:

$$r = b + a|\sin\theta| + z(\theta) \quad (1),$$

where b is the minor radius, a is the major radius minus the minor radius, and z is the correction factor.

With reference again to FIG. 1, a $\theta$ or angular position clock 70 clocks or increments the angular position $\theta$ of the camera head. The angular position may change in steps or increments with the camera head resting at each step for a short duration or may move continuously. The continuous movement embodiment has less dead time; whereas, the incremental movement embodiment has less of a tendency for the image to blur. A sine determining means 72 determines the sine of each angle $\theta$. A multiplying means 74 multiplies the sin $\theta$ term by the major and minor diameter difference term, a from a subtraction or difference means 76. A first adding means 78 adds the minor radius b to the a sin$\theta$ term.

Each $\theta$ value from the angular position clock means 70 addresses the enabled one of the correction factor tables 64 to retrieve the z($\theta$) correction term. An adding means 80 adds the z correction term to define the radius between the center of rotation and the camera head. A control means 82 receives the radius signal from the adding means 80 and the $\theta$ signal from the $\theta$ clock 70 and resolves the appropriate x and y coordinate positions of the detector head, and the appropriate angular position $\theta$ of the camera head. The control means controls the positioning means 10, 12, and 14 to control the position of the camera head as it moves through the orbit. Optionally, the position resolving means may include a comparing means which compares the x, y, and $\theta$ position indicated by the control means with the monitored x, y, and $\theta$ positions from the x and y monitoring means 40 and 42 and the angular position clock 70 to create a feed back or servo loop.

In the preferred embodiment, the values of z are different for a top half 66a of the orbit above the patient table 20 and a bottom half 66b of the orbit below the patient table 20. More specifically to the preferred embodiment, the value of z is substantially zero above the patient table such that the camera head moves substantially along the selected generally ellipsoidal orbit or loop 66a. The z value becomes non-zero in the lower half of the orbit to expand the radius just enough to clear the patient table. Normally, the z value would have a maximum at the angle extending from the center of rotation through the edge or corner of the patient table. The z values, however, will increase non-linearly as the size of the subject increases. In this manner, the shape of the orbit as well as its size changes as a function of a characteristic, specifically, the size or aspect ratio, of the subject.

Of course, it is to be appreciated that the addition of the correction factor z may be added to other equations which describe the orbit, such as an ellipse, a circle, or the like. As yet another alternative, the value of z might be calculated on the fly rather than stored in a look-up table. The value of z for each angular increment may be calculated based on the position of the corner of the patient table and the characteristics of the camera head.

The invention has been described with reference to the preferred embodiments. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A tomographic camera system comprising:
   a camera head for receiving radiation from a subject and producing output signals indicative thereof;
   a gantry means for movably supporting the camera head for controlled movement about the subject;
   a gantry control means for controlling movement of the camera head along a path of a selected size and a selected shape around the subject;
   a path altering means for automatically altering the path shape in accordance with a characteristic of the subject; and,
   a subject characteristic indicating means for indicating the subject characteristic.

2. The system as set forth in claim 1 wherein the path altering means includes a memory means for storing path shape alterations and means for combining the path shape alterations with signals indicative of a selected path shape, the memory means being selectively addressed by the subject characteristic for retrieving a corresponding subset of the path shape alterations.

3. The system as set forth in claim 1 wherein the path shape and size are defined by a generally ellipsoidal loop plus a correction factor, which correction factor varies with angular position around the loop.

4. The system as set forth in claim 3 further including a memory for storing the correction factor, which correction factor memory is addressed by the subject characteristic and angular positions of the camera head as it moves around the path.

5. The system as set forth in claim 1 wherein the characteristic indicating means including means for determining major and minor axes of a closed loop path around the patient, whereby the subject characteristic includes the major and minor axes.

6. The system as set forth in claim 5 further including a comparing means for comparing a function of the major and minor axes with preselected standards and selecting a table of correction factors in accordance with the comparison.

7. The system as set forth in claim 6 wherein the gantry control means includes means for determining a radius of rotation at angular positions around a closed loop and means for combining the radius with a correction factor retrieved from the correction factor tables.

8. The system as set forth in claim 7 wherein the correction factor tables are stored in a correction factor memory means and further including an angular position clock means for indicating the angular position of the camera head around the closed loop, the correction factor memory means being addressed by the angular position clock means to retrieve corresponding correction factors.

9. The system as set forth in claim 1 further including tomographic reconstruction means for reconstructing a tomographic image representation from the output signals.

10. A method of tomographic scanning comprising:
    measuring a characteristic indicative of a size and shape relative to a first patient portion to be imaged;
    detecting radiation from the prior patient portion at a plurality of locations therearound, which locations define a first path of a first size and first shape selected in accordance with the first measured patient portion characteristic;
    reconstructing a first tomographic image representation from the collected radiation;
    measuring the characteristic relative to a second patient portion to be imaged;
    detecting radiation from the patient portion at a plurality of locations along a second path with a second size and second shape selected in accordance with the second measured patient characteristic such that the second path shape and size are both adjusted in accordance with the second measured patient characteristic; and,
    reconstructing a second tomographic image representation from the radiation detected along the second path.

11. The method as set forth in claim 10 wherein the first and second paths are defined by a generally ellipsoidal loop combined with location dependent correction factors.

12. The method as set forth in claim 11 wherein the correction factors are stored in a table and further including at each of a plurality of locations along the first and second paths, accessing the table to determine each location dependent correction factor for modifying the generally ellipsoidal loop.

13. The method as set forth in claim 11, wherein the correction factors are stored in a plurality of tables, each table corresponding to a different value of the measured characteristic and further including in response to measuring the characteristic, selecting the corresponding one of the tables.

14. The method as set forth in claim 10 wherein the steps of measuring the characteristics include measuring major and minor axes of the patient and a supporting structure thereunder.

15. The method as set forth in claim 14 wherein the step of determining the characteristics further includes comparing the measured major and minor axes, the relationship between the major and minor axes being the characteristic.

* * * * *